United States Patent [19]

Clauss et al.

[11] Patent Number: 4,876,046

[45] Date of Patent: Oct. 24, 1989

[54] SUBSTITUTED GLUTARIC AND ADIPIC DIPEROXYACIDS

[75] Inventors: Allen D. Clauss, Fairfield; Eugene P. Gosselink, Cincinnati, both of Ohio

[73] Assignee: The Procter & Gamble Company, Cincinnati, Ohio

[21] Appl. No.: 353,182

[22] Filed: May 11, 1989

Related U.S. Application Data

[63] Continuation of Ser. No. 80,142, Jul. 29, 1987, abandoned, which is a continuation of Ser. No. 744,597, Jun. 14, 1985, abandoned.

[51] Int. Cl.$^4$ .............................................. C07C 179/00
[52] U.S. Cl. ................................... 8/111; 252/186.76; 562/2
[58] Field of Search ................ 260/502 R; 252/186.26

[56] References Cited

U.S. PATENT DOCUMENTS 3,585,176  6/1971  Gerritsen et al. ............... 260/502 R
4,487,723  12/1984  Mayer ............................. 260/502 R Primary Examiner—Bruce Gray
Attorney, Agent, or Firm—Robert B. Aylor; Richard C. Witte

[57] ABSTRACT

Novel peroxyacids of the formula:

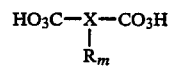

wherein X is an alkylene group selected from propylene and butylene, R is alkyl containing from 4 to 12 carbon atoms, benzyl or phenyl and m is 1 or 2. The compounds are useful as disinfectants and fabric bleaches.

3 Claims, No Drawings

SUBSTITUTED GLUTARIC AND ADIPIC DIPEROXYACIDS

This is a continuation of application Ser. No. 07/080,142, filed July 29, 1987 abandoned; which is a continuation of application Ser. No. 06/744,597, filed June 14, 1985, now abandoned.

FIELD OF THE INVENTION

This invention pertains to certain novel alkyl and phenyl-substituted diperoxy glutaric and adipic acids which have utility as oxidizing agents, particularly in the bleaching of fabrics.

BACKGROUND OF THE INVENTION

The bleaching properties and disinfectant properties possessed by oxidizing agents are well known. The most common types of oxidizing agents used for bleaching and disinfecting are chlorine (e.g., hypochlorites and chloramines); hydrogen peroxide and other peroxy compounds; chlorite and chlorine dioxide.

The need for improved oxidizing agents for disinfecting and bleach use is increasing in view of energy conservation and environmental protection measures. For example, in the detergent industry improved cleansing of fabrics is being sought since washing performance has suffered because of lower wash temperatures, reduced use of phosphate builders and increased use of synthetic fabrics. The use of improved oxidizing agents for bleaching is an effective way to restore this lost performance.

A number of peroxy compounds have been evaluated as bleaching agents and some of these have been diperoxy acids. For example, U.S. Pat. Nos. 3,959,163, Farley, issued May 25, 1976, and 4,094,808, Stewart et al., issued June 13, 1978, disclose bleach compositions where the active agent is disperisophthalic acid; U.S. Pat. No. 4,134,850, McCrudden et al., issued Jan. 16, 1979, discloses bleaching compositions where the active agents is a cycloaliphaticdiperoxy acid; and U.S. Pat. Nos. 2,813,896, Krimm, issued Nov. 19, 1957, and 4,126,573, Johnson, issued Nov. 21, 1978, disclose bleaching utility for alpha omega long chain aliphatic diperoxy acid.

U.S. Pat. Nos. 4,487,723, Mayer, issued Dec. 11, 1984, and 4,391,725, Bossu, issued July 5, 1983, disclose certain alkyl and/or phenyl-substituted diperoxy succinic acids and their use as fabric bleaches.

Although satisfactory results are achieved using the diperoxy acids disclosed in various of the foregoing references, there remains a need for new and structurally different diperoxy acids to satisfy specialized applications in home laundry bleaching and in disinfecting. Hence, those skilled in the art of bleach and disinfectant composition formulation are constantly looking for new and improved peroxy compounds for use as in such formulations. The present invention provides to the art a group of novel diperoxy acids which are highly suitable for use in bleaching and/or disinfecting compositions.

SUMMARY OF THE INVENTION

The present invention is directed to novel peroxyacids having the formula:

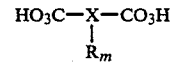

wherein X is an alkylene group selected from propylene and butylene, R is alkyl containing from 4 to 12 carbon atoms or phenyl and m is 1 or 2.

DETAILED DESCRIPTION OF THE INVENTION

In accordance with the present invention it has been found that certain substituted diperoxy glutaric and adipic acids are highly suitable oxidizing agents for use as laundry bleaching agents. They are also suitable for disinfectant use.

The compounds of the invention have the general formula

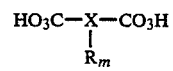

wherein X is a propylene (i.e., $-CH_2CH_2-CH_2-$) or butylene (i.e., $-CH_2CH_2CH_2CH_2-$) group and R is an alkyl (acyclic or cyclic) group containing from about 4 to about 12 (preferably from about 6 to about 8) carbon atoms, benzyl or phenyl, substituted onto said propylene or butylene group, and m is 1 or 2. Preferably m is 1. When X is propylene the compounds are substituted diperoxyglutaric acids and when X is butylene the compounds are substituted diperoxyadipic acids. Exemplary compounds are β-hexyldiperoxyglutaric acid, β-cyclohexyldiperoxyglutaric acid, β-octyldiperoxyglutaric acid, α-decyldiperoxyglutaric acid α-heptyldiperoxyglutaric acid, α-phenyldiperoxyglutaric acid, β-phenyldiperoxyglutaric acid, α-benzyldiperoxyglutaric acid, α-t-butyldiperoxyadipic acid, α-pentyldiperoxyadipic acid, α-octyldiperoxyadipic acid, α-decyldiperoxyadipic acid, α-phenyldiperoxyadipic acid, α-cyclohexyldiperoxyadipic acid, α-benzyldiperoxyadipic acid, β-hexyldiperoxyadipic acid, β-octyldiperoxyadipic acid, β-t-octyldiperoxyadipic acid, β-dodecyldiperoxyadipic acid, β-phenyldiperoxyadipic acid, β,β-dihexyldiperoxyglutaric acid, β-methyl-β-hexyldiperoxyglutaric acid and β-ethyl-β-octyldiperoxyglutaric acid.

The compounds of the invention exhibit a unique combination of surface activity, water solubility and chemical stability in aqueous solution which has not been observed in other peroxy-acids. The compounds are particularly effective bleaching agents for use in hard water.

The presence of hydrophobic substituent groups and hydrophilic percarboxy groups in the same molecule renders the molecule surface active, thereby causing, in an aqueous solution, a concentration of the diperoxyacid molecules at the surface of the sustrate (e.g., fabric) being treated with the solution. It is believed that the 3-4 carbon-atom spacing between the percarboxy groups in these compounds, in combination with the preferred alkyl chain lengths, is about optimal for achieving maximum surface activity while retarding formation of micelles. Micellization of the diperoxyacid compounds in solution tends to inhibit concentration of the compounds at substrate surfaces and promotes nonproductive decomposition in solution, thereby reducing bleaching and/or disinfecting efficiency.

The compounds of the invention are solids at room temperature and therefore can conveniently be formulated in granular compositions such as laundry granules.

The peroxyacids of the invention can be made by oxidation of the parent dicarboxylic acids by known oxidation techniques, such as by hydrogen peroxide in either a water/sulfuric acid or water/methanesulfonic acid solvent system. See U.S. Pat. Nos. 4,119,660, Hutchins, issued Oct. 10, 1978; 4,233,235, Camden et al., issued Nov. 11, 1980; 4,244,884, Hutchins, issued Jan. 13, 1981; and 4,487,723, Mayer, issued Dec. 11, 1984, all incorporated by reference herein.

The parent dicarboxylic acids can be made by known synthetic techniques. Some examples are given below.

α-alkylglutaric acids can be prepared by malonic ester synthesis techniques. See J. C. Roberts et al., *J. Chem. Soc.* p. 2482 (1950), incorporated byy reference herein. The following reaction sequence is followed:

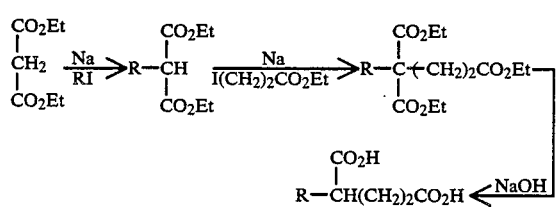

In preparing the α-alkyladipic acids the same procedure is followed, except that in the second step, I(CH$_2$)$_3$CO$_2$Et is used as the substituting agent instead of I(CH$_2$)$_2$CO$_2$Et. Benzyl iodide can be used in place of alkyl iodide in the first step to prepare the corresponding benzyl-substituted diacids.

α-phenyl glutaric acids and α-phenyladipic acids can be made by the same procedure as α-alkylglutaric acids and α-alkyladipic acids except that in the first step phenyl iodide is used as the substituting agent instead of alkyl iodide. Alternatively, the phenyl-substituted glutaric and adipic acids can be made by using the procedure described in *Org. Syn.* 16 (1936), 33; *Coll. Vol. II* (1943), 288 (incorporated by reference herein) to prepare the diester of the first step.

β-monosubstituted alkylgutaric acids can be prepared by the procedure described by Day et al., *J. Chem. Soc.* 117, p. 1465 (1920), incorporated by reference herein. In this procedure cyanoacetamide is reacted with an aldehyde, followed by acid hydrolysis.

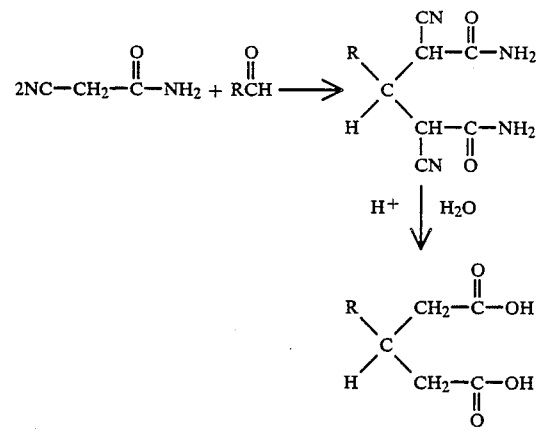

β,β-dialkyl glutaric acids can be prepared by the procedure described by Handley et al., *Aust. J. Chem.*, 13, p. 129 (1960), incorporated by reference herein. In this procedure, ethylcyanoacetate is reacted with a dialkyl ketone in the presence of ammonia, followed by acid hydrolysis.

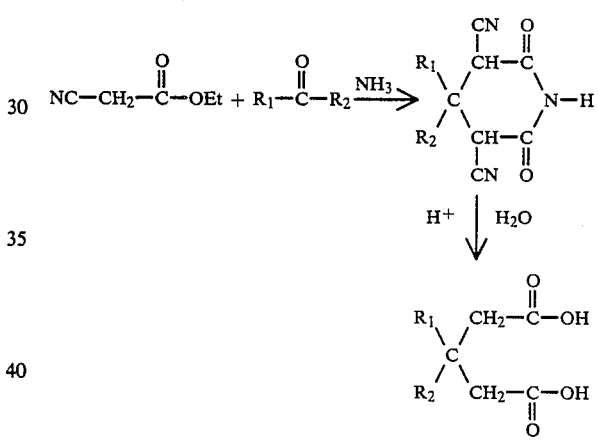

β-alkyladipic acids can be prepared by the procedure described by Goheen et al., *J. Org. Chem.*, 53, p. 891 (1958), incorporated by reference herein. In this procedure an acyl chloride is reacted with phenol in the presence of aluminum chloride to form the ortho and para acylsubstituted phenol. The para isomer is then isolated by distillation and subjected to Clemenson reduction in the presence of Zn/HCl to convert the acyl phenol to the corresponding alkyl phenol. The alkyl phenol is then converted to the corrsponding alkyl cyclohexanol by reduction with hydrogen. The alkyl cyclohexanol is then oxidized by nitric acid in the presence of ammonium vanadate to form the β-alkyladipic acid.

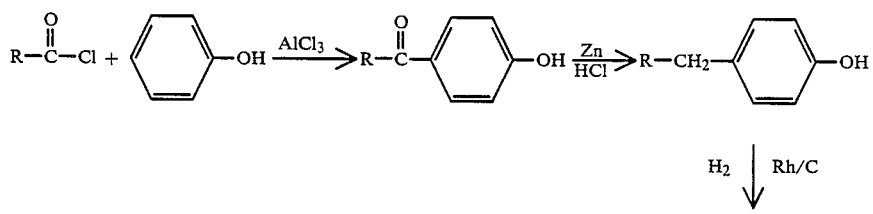

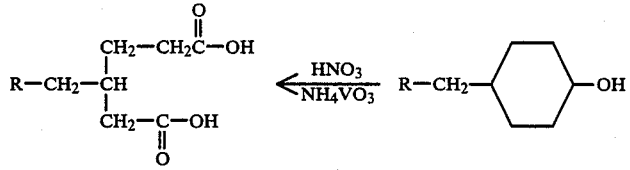

The substituted diperoxy acids of the invention are conveniently employed as the primary bleaching agent in the form of particulate solids in granular or powder formulations containing diluents and stabilizers which retard the loss of available oxygen which can occur due to exothermic decomposition when exposed to elevated temperatures, or catalytic decomposition when exposed to heavy metal ions.

Suitable stabilizers to prevent exothermic decomposition of these compounds are those which are capable of liberating moisture at a temperature below the composition of the particular substituted-diperoxyacid compound. A wide variety of exotherm control materials can be used and include hydrated materials, such as potassium aluminum sulfate dodecahydrate, magnesium sulfate heptahydrate, sodium aluminum sulfate dodecahydrate, magnesium ammonium sulfate hexahydrate, and acids, such as boric acid. Boric acid is the preferred exotherm stabilizer (See U.S. Pat. No. 4,100,095, Hutchins, issued July 11, 1978, incorporated by reference herein).

Suitable stabilizers to prevent catalytic decomposition of the instant compounds in the presence of heavy metals, for example, iron and copper, are chelating agents. Suitable chelating agents are alkali metal polyphophates such as tetrasodium pyrophosphate and disodium acid pyrophosphate, 8-hydroxyquinoline, ethylenediamine tetra acetic acid, 1-hydroxy-ethylidene diphosphonic acid, aminotri (methylene phosphonic acid), phosphoric acid and mixtures thereof. Phosphoric acid or a mixture of phosphoric acid and terasodium pyrophosphate is preferred.

In addition to the chelating agents and exotherm control agents mentioned above, coating materials can also be used to extend the shelf life of dry formulations containing the substituted diperoxyacid compounds of this invention as the primary bleaching agent. Suitable coating materials include a wide variety of fatty acids, fatty alcohols, derivatives thereof, such as esters and ethers, derivatives of polyethylene glycols, such as esters and ethers, hydrocarbon oils and waxes. These materials not only aid in preventing moisture from reaching the diperoxyacid compound, but can also be used to segregate the diperoxyacid from other agents which may be present in the formulation and adversely affect the stability of the diperoxyacid.

Coating of the diperoxyacid particles with a surfactant such as the alkali metal salt of an alkylbenzene sulfonate having from 10 to 14 carbon atoms in the alkyl group, a $C_9$-$C_{22}$ alkyl sulfonate or a $C_9$-$C_{22}$ alkyl sulfate, can be employed to improve the water solubility properties of the diperoxyacid particles. See for example U.S. Pat. No. 4,126,573, Johnson, issued Nov. 21, 1978, incorporated by reference herein.

A diluent is optionally employed as a processing aid with the diperoxyacids herein to adjust the concentration of the peroxyacid and to facilitate handling, shipping and subsequent addition to the wash water, or to facilitate blending the diperoxyacid with additional detergent materials such as surfactants, builders, antistatic agents, coloring agents, bleach activators, perfumes and the like to form granular detergent-bleach compositions. The diluent or processing aid can conveniently be used in an amount to provide a formulation containing from about 30 to 60 percent by weight of the active diperoxyacid, from about 1 to 5 percent by weight chelating agent, from about 15 to 55 percent by weight exotherm control agent. A preferred diluent is sodium sulfate, which is compatible with the diperoxyacids and stabilizers, as well as with ingredients in detergent formulations.

Compositions containing the diperoxyacids of the invention should contain as little free moisture as possible, since presence of free moisture is detrimental to storage stability of the diperoxyacids. Preferably, the moisture level should be less than 1% of the composition.

In the bleaching of fabrics with the peroxyacids of the present invention, the fabrics are contacted with an aqueous solution containing an amount of the peroxyacid sufficient to provide at least about 2 ppm and preferably from about 6 to about 20 ppm available oxygen in the solution.

The invention will be further illustrated by the following examples.

EXAMPLE I

Preparation of β-t-octyladipic Acid 4-t-octylphenol (250 g, used as received from Rohm and Haas), methanol (250 ml), acetic acid (2.5 ml) and rhodium on carbon catalyst (5.0 g, 5% rhodium, MCB Chemicals) were added to a 3 L glass lined autoclave. The autoclave was charged to 60 psig $H_2$ and heated at 60° C. until hydrogen uptake was complete (about 10 hrs.). The mixture was cooled to room temperature and the catalyst was removed by filtration in a glove bag under a nitrogen atmosphere (CAUTION: pyrophoric catalyst). The solvent was removed on a rotary evaporator and the residue was dissoved in dichloromethane and extracted with 10% sodium carbonate solution (3×250 ml) to remove phenolic contamination, thus avoiding the formation of a yellow impurity in the subsequent oxidation step. The dichloromethane solution was washed with 25% sulfuric acid (2×100 ml) distilled water (1×250 ml), and dried over anhydrous magnesium sulfate, after which the solvent was evaporated to isolate 4-t-octylcyclohexanol as a low melting off-white solid (182 g, 81%).

70% nitric acid (330 g) and distilled water (140 ml) were added to a 1 L 3-neck flask equipped with a water cooled condenser, a mechanical stirrer and a thermometer. The solution was heated to 80° C. and ammonium vanadate (1 g) was added which caused a color change from colorless to dark red to yellow. A small portion (about 1 g) of 4-t-octylcyclohexanol was added to initiate the reaction evidenced by evolution of brown $NO_2$ gas after which external heating was discontinued and the remainder of the 4-t-octylcyclohexanol (249 g) was added in small portions at a rate to maintain the temperature at 80°-90° C. (4 hr. addition period). The mixture was refluxed until the $NO_2$ evolution subsided (about 24 hrs.). Upon cooling, a yellow pasty mass separated which was isolated and washed free of nitric acid with distilled water. The mass was dissolved in dichloromethane (1 L) and washed with 25% sulfuric acid (3×150 ml) followed by distilled water (2×200 ml). Removal of the solvent on a rotary evaporator provided a yellow solid which was recrystallized from toluene to afford β-t-octyladipic acid as a white solid (195 g, 64% yield; mp 135°-137° C., Lit. 136°-137° C.; acid value 429.6, theoretical 434).

EXAMPLE II

Preparation of β-n-Hexyladipic Acid

A stirred suspension of 4-n-hexylphenol (972 g; 5.46 mol), 61.7 g of 5% rhodium on carbon catalyst (46.0 g of Alfa Chemical Co. lot 063081 and 17.7 g of MCB Chemicals lot A12M04), HOAc (21 ml), and MeOH (5.0 L) was hydrogenated in a 5 gallon autoclave (100 psi) at 35°-55° until 73% of theoretical $H_2$ was consumed. A sample was withdrawn and NMR and GC tests showed that a small amount of the hexylphenol remained. Hydrogenation was continued until a total of 78% of theoretical $H_2$ was consumed. The catalyst was filtered off, and the clear filtrate was concentrated in vacuo to a clear oil, 1065 g (106%); IR (neat) $cm^{-1}$ 3400, (OH) 1715 (carbonyl); NMR ($CDCl_3$) no aromatic absorbance was observed.

The amounts described in the following paragraph represent total quantities used for the sum of two identical side-by-side reactions (CAUTION: strong exotherm potential).

A stirred solution of 50% aqueous $HNO_3$ (2.3 L) and $NH_4VO_3$ (900 mg) was heated to 95° then cooled to 70°. The heating mantle was replaced with a cooling bath then 4-n-hexylcyclohexanol (1002 g apparent amount; 946 g corrected to 100% versus 106%) was added dropwise during 3 hours. During the addition the internal temperature was maintained between 60°-70°. After the addition was complete, the reaction mixture was stirred at 65°-70° for 5 hours then stored at room temperature for 16 hours. The precipitated solid was collected on a filter, washed with $H_2O$, then dissolved in $Et_2O$ (5.0 L). The organic solution was washed with $H_2O$ (3×2 L), dried over $Na_2SO_4$, then concentrated in vacuo to an oil. This material was vacuum distilled to give 870 g (73%) of partially purified product; bp 190°-210° (0.4-0.7 torr). The distillate crystallized upon cooling. This material was recrystallized from warm (60°) benzene-hexane (1.1 L:8.0 L) followed by pulverization and screening to give 582 g (67% recovery) of purified β-n-hexyladipic acid as white crystals; mp 70°-71°; literature mp 71°-72°. IR (Nujol Mull) $cm^{-1}$ 3400-3000 (broad absorbance for $-CO_2H$); 2800-2500 ($-CO_2H$); 1700 (carbonyl). NMR ($CDCl_3$) δ11.85 (s, 2H, $-CO_2H$; 2.60-2.15 (m, 4H, $$-CH_2\underset{\underset{O}{\|}}{C}-);$$

2.00-0.70 (16H, $-CH-$, $-CH_2-$, and $-CH_3$).

EXAMPLE III

Preparation of β-n-heptylglutaric Acid

Cyanoacetamide (202 g, 2.4 mol) and distilled water (800 ml) were added to a 3 L 3-neck flask fitted with a mechanical overhead stirrer, thermometer and addition funnel. Octanal (154 g, 1.2 mol) was added from the addition funnel over a period of 10 minutes followed by piperidine (6 ml) added at once. The solution was stirred at room temperature. Over a period of 30 minutes at room temperature the solids slowly dissolved leaving a clear greenish solution. After a period of 50 minutes white solid began to precipitate from solution resulting in a thick white slurry after 6 hours a room temperature. After 22 hours, the mixture was suction filtered. The resultant solid was returned to the flask and 1 L of 50% aqueous hydrochloric acid was added. The mixture was heated at reflux for 19 hours at which time an aliquot was removed, extracted with diethyl ether and the ether extract in turn was extracted with 10% sodium carbonate. After acidification with concentrated HCl and reextraction into ether, the resultant base-soluble fraction was analyzed by HPLC ($C_{18}$ODS column, 66% methanol) and found to contain a large number (greater than 10) of components. After 115 hours of heating at reflux, the base-soluble extract analyzed by HPLC as one major component (81%). Upon cooling, the reaction mixture separated into a red organic upper layer and a colorless aqueous lower layer. The aqueous layer was extracted with ether (300 ml). The ether extract was combined with the organic layer and the whole was extracted with 10% $Na_2CO_3$ (4×200 ml). The aqueous extract was then acidified which resulted in separation of a dark oil (249 g, 90%; acid value 279, theoretical acid value 487). The oil was dissolved in hexane, cooled in a dry ice bath with rapid stirring which resulted in precipitation of white hygroscopic crystalline product (131 g, 46%; acid value 485.9; mp 43°-44° C.).

EXAMPLE V

β-t-octyldiperoxyadipic Acid

β-t-octyladipic acid (86.1 g, 0.33 mol) was powdered using a mortar and pestle and added to a beaker containing 98% methanesulfonic acid. The resultant suspension was cooled to 20° C. and 70% hydrogen peroxide was added slowly with constant stirring to maintain the temperature just below 40° C. After the addition was complete (about one-half hour) the suspension was stirred at room temperature for 1 hour after which the resultant clear solution was poured into 500 ml of cold distilled water, and extracted with dichloromethane (3×100 ml). The dichloromethane solution was washed with distilled water (2×50 ml), dried over anhydrous magnesium sulfate after which the solvent was removed on a rotary evaporator to provide a clear oil. Storage of the oil in a stoppered flask overnight at 0.5° C. resulted in crystallization of β-t-octyldiperoxyadipic acid as a white brittle solid (83.4 g,; mp 60°-62° C.; % AvO=9.3, theory 11.0; HPLC, $C_{18}$ ODS column, 70% methanol solent, retention time: 6.3 min., diperoxy-acid, relative peak area 76%; 7.4 min, monoperoxyacid, relative peak area 24%.

Yield of β-t-octyldiperoxyadipic acid= 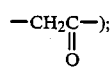

$$\frac{83.4 \text{ (actual \% AvO)}}{\frac{\text{theoret. \% AvO}}{\text{DPA}} + \frac{24}{26} \frac{\text{theoret. \% AvO}}{\text{MPA}}} =$$

$$\frac{83.4 \ (9.3)}{11.0 + (24/76)(5.8)} = 60.49 \text{ g}$$

$$\% \text{ yield} = \frac{60.4 \text{ g } (100)}{95.7 \text{ g}} = 63\%$$

EXAMPLE V

Preparation of β-n-hexyldiperoxyadipic Acid

Attempted peroxidation of β-n-hexyladipic acid prepared as described in Example II resulted in an uncontrollable exothermic reaction. Thus, it was necessary to further purify the starting material before it could be successfully peroxidized. β-n-hexyladipic acid, (100 g) was dissolved in dichloromethane (500 ml) and washed with 25% sulfuric acid (3×150 ml), 5% sodium bicarbonate (3×100 mls), and distilled water (2×100 ml). The dichloromethane solution was dried over anhydrous magnesium sulfate after which the solvent was removed on a rotary evaporator leaving a clear oil which was crystallized from hexane to afford a white waxy solid (76.4 g). The purified β-n-hexyladipic acid (70.0 g, 0.304 mol) and 98% methanesulfonic acid (149 g, 1.55 mol) were added to a beaker and cooled to 15° C. 70% hydrogen peroxide (59.14 g, 1.74 mol) was added at a rate which maintained the temperature of about 30° C. while constantly stirring the suspension using a magnetic stirrer. After the addition was complete (about 10 minutes), the suspension was stirred at room temperature for an additional 1 hour, 50 minutes, which resulted in a clear solution. The solution was poured into cold distilled water (500 ml) and extracted with dichloromethane (1×300 ml, 2×250 ml). The dichloromethane solution was in turn extracted with 5% sodium sulfate solution 1×300 ml, 2×200 ml), dried over anhydrous magnesium sulfate after which the solvent was removed on a rotary evaporator. The oily residue was recrystallized from toluene to yield β-n-hexyldiperoxyadipic acid as a powdery white solid (49.7 g, mp 51.5°-52.5° C.; %AvO=11.6, theory=12.2; HPLC, $C_{18}$ODS column, 67% methanol solvent, retention time: 5.84 minutes, diperoxy acid, relative peak area 96%, 10.00 min, diacid, relaive peak area 4%).

Yield of β-hexyldiperoxyadipic acid=11.6/12.2 (49.7)=47.25

$$\% \text{ Yield} = \frac{47.25 \ (100)}{79.6} = 59\%.$$

EXAMPLE VI

Preparation of β-n-heptyldiperoxyglutaric Acid

β-n-heptylglutaric acid (85 g, 0.36 mol) was added to an 800 ml beaker along with 98% methansulfonic acid (176 g, 1.84 mol) and the mixture was cooled to 10° C. 70% hydrogen peroxide was added slowly with constant stirring to maintain a reaction temperature of about 30° C. After the addition was complete, the solution was stirred at room temperature for 2 hours. Workup as described for the alkyldiperoxyadipic acids provided β-n-heptyldiperoxyglutaric acid as an oil which solidified upon cooling to 0° C. but was found on rewarming to have a melting point of 19°-22° C. (yield 93 g; %AvO=10.7, theory=12.2; HPLC, $C_{18}$ODS column, 67% methanol, retention time: 6.3 minutes, diperoxyacid, relative peak area 87%, 7.6 minutes, monoperoxyacid, relative peak area 13%.).

Yield of β-hexyldiperoxyglutaric acid=

$$\frac{93 \ (10.7)}{12.2 + 13/87 \ (6.5)} = 75.6$$

$$\% \text{ Yield} = \frac{76 \ (100)}{94} = 81\%.$$

EXAMPLE VII

Preparation of Stabilized Soluble Bleach Granules Containing β-n-hexyldiperoxyadipic Acid A bleach granule was prepared which had the following composition:

| Chemical | % |
| --- | --- |
| β-hexyldiperoxyadipic acid | 9.29 |
| β-hexyladipic acid | 0.37 |
| $C_{13}$ linear alkylbenzene sulfonate | 4.82 |
| Boric acid | 12.56 |
| Tetrasodium pyrophosphate | 0.038 |
| Phosphoric acid | 0.028 |
| Dipicolinic acid | 0.028 |
| Sodium sulfate | 69.85 |
| Moisture | 3.00 |
|  | 99.98% |

$C_{13}$ LAS paste (124.0 g, 31.4% $C_{13}$ LAS, 15% $Na_2SO_4$, balance water) was added to a stainless steel minicrutcher maintained at 100° F. Tetrasodium pyrophosphate, (0.306 g), phosphoric acid (0.230 g), dipicolinic acid (0.230 g), and water (227.8 g) were added and the paste was blended to a uniform consistency. Boric acid (101.4 g), β-n-hexyldiperoxyadipic acid (78.0 g, 11.73% AvO), and sodium sulfate (545.2 g) were added and the mixture was again blended to a uniform consistency. The crutcher mix was then spread on a tray and cooled to ca 40° F. after which it was forced through a 20 mesh nylon screen and the resultant granules were dried at 80° F., 15% relative humidity overnight. After drying, the granules contained 3% free moisture and had an available oxygen conent of 1.0% (Theory 1.1%).

The bleach granules were used in combination with recommended amounts of typical laundry detergents to bleach a variety of stains and dingy clothing articles. Excellent bleaching performance was observed when the bleach granules were added at a level of 96 grams to 64 liters of wash water thereby providing 15 ppm AvO in the wash solution.

What is claimed is:

1. β-n-hexyldiperoxyadipic acid.
2. The method of bleaching fabrics comprising the step of contacting said fabrics with an aqueous solution comprising an effective amount of β-n-hexyldiperoxyadipic acid.
3. The method of claim 2 wherein said β-n-hexyldiperoxyadipic acid supplies at least about 2 ppm available oxygen in said solution.

* * * * *